United States Patent
Zaaroor Regev et al.

(10) Patent No.: US 10,688,070 B2
(45) Date of Patent: Jun. 23, 2020

(54) SERINE GLYCEROPHOSPHOLIPID PREPARATION AND METHOD FOR TREATMENT OF SEIZURES

(71) Applicants: Daphna Zaaroor Regev, Nofit (IL); Yael Herzog, Gesher HaZiv (IL); Robert Chudnow, Plano, TX (US); Yael Richter, Kibutz Sarid (IL); Gali Olga Soria Artzi, En-Harod Ihud (IL)

(72) Inventors: Daphna Zaaroor Regev, Nofit (IL); Yael Herzog, Gesher HaZiv (IL); Robert Chudnow, Plano, TX (US); Yael Richter, Kibutz Sarid (IL); Gali Olga Soria Artzi, En-Harod Ihud (IL)

(73) Assignee: ENZYMOTEC LTD., Migdal Haemeq (IL)

( * ) Notice: Subject to any disclaimer, the term of this patent is extended or adjusted under 35 U.S.C. 154(b) by 93 days.

(21) Appl. No.: 15/039,741

(22) PCT Filed: Dec. 5, 2014

(86) PCT No.: PCT/US2014/068833
§ 371 (c)(1),
(2) Date: May 26, 2016

(87) PCT Pub. No.: WO2015/085192
PCT Pub. Date: Jun. 11, 2015

(65) Prior Publication Data
US 2016/0374974 A1    Dec. 29, 2016

Related U.S. Application Data

(60) Provisional application No. 61/912,073, filed on Dec. 5, 2013.

(51) Int. Cl.
| | |
|---|---|
| A61K 31/202 | (2006.01) |
| A61K 31/685 | (2006.01) |
| A61K 47/54 | (2017.01) |
| A61K 31/19 | (2006.01) |
| A61K 31/216 | (2006.01) |
| A61K 31/423 | (2006.01) |
| A61K 31/513 | (2006.01) |
| A61K 31/55 | (2006.01) |
| A61K 31/5513 | (2006.01) |
| A61K 45/06 | (2006.01) |
| A61K 47/24 | (2006.01) |

(52) U.S. Cl.
CPC ............ *A61K 31/202* (2013.01); *A61K 31/19* (2013.01); *A61K 31/216* (2013.01); *A61K 31/423* (2013.01); *A61K 31/513* (2013.01); *A61K 31/55* (2013.01); *A61K 31/5513* (2013.01); *A61K 31/685* (2013.01); *A61K 45/06* (2013.01); *A61K 47/24* (2013.01); *A61K 47/542* (2017.08); *A61K 47/544* (2017.08)

(58) Field of Classification Search
None
See application file for complete search history.

(56) References Cited

U.S. PATENT DOCUMENTS

| | | |
|---|---|---|
| 6,005,004 A | 12/1999 | Katz et al. |
| 2009/0074857 A1 | 3/2009 | Dror et al. |
| 2011/0301238 A1 | 12/2011 | Borges |

FOREIGN PATENT DOCUMENTS

| | | |
|---|---|---|
| JP | 1994-040902 A | 2/1994 |
| JP | 2002-535355 A | 10/2002 |
| JP | 2012-102070 A | 5/2012 |
| WO | 2000/044361 A2 | 8/2000 |
| WO | 2005/037848 A2 | 4/2005 |
| WO | 2005/038037 A2 | 4/2005 |
| WO | 2009/156991 A2 | 12/2009 |

OTHER PUBLICATIONS

International Search Report, dated Mar. 3, 2015, issued in corresponding International Application No. PCT/US2014/068833.
Pasqui, L. et al., "Effects of Phophatidylserine in an Experimental Model of Generalized Epilepsy", Rivista di Neurologia (1984); vol. 54:1, pp. 128-138. (English translation attached).
Yuen, A. et al., "Omega-3 Fatty Acid Supplementation in Patients with Chronic Epilepsy: A randomized Trial", Epilepsy and Behavior (2005); vol. 7:2; pp. 253-258.
European Extended Search Report dated Jul. 19, 2017 from counterpart European Application No. 14867329.6.

*Primary Examiner* — James D. Anderson
*Assistant Examiner* — Stephanie K Springer
(74) *Attorney, Agent, or Firm* — Fox Rothschild LLP

(57) ABSTRACT

A preparation for treatment and/or prevention of seizures comprising a non-mammalian derived mixture of serine glycerophospholipids (PS) conjugates, wherein the mixture comprises (a) Eicosapentaenoic acid (EPA) conjugated to PS and (b) Docosahexaenoic acid (DHA) conjugated to PS, and methods of treatment of seizures with same.

21 Claims, No Drawings

SERINE GLYCEROPHOSPHOLIPID PREPARATION AND METHOD FOR TREATMENT OF SEIZURES

CROSS-REFERENCE TO RELATED APPLICATIONS

This application is a national stage application of International Application No. PCT/US2014/068833, filed Dec. 5, 2014, claims priority of U.S. Provisional Application No. 61/912,073, filed Dec. 5, 2013, the entire contents of which are hereby incorporated by reference herein.

FIELD OF THE INVENTION

The present invention relates to a preparation comprising a mixture of serine glycerophospholipid derivatives and a method for treatment of seizures by administering such a preparation.

BACKGROUND OF THE INVENTION

Seizures represent a clinical manifestation of an abnormal and excessive excitation and synchronization of cortical neurons. The clinical manifestation of a seizure consists of sudden and transitory abnormal phenomena which may include alterations of consciousness, motor, sensory, autonomic, or psychic events perceived by the patient or an observer.

Seizures disorders can be associated with abnormal electrical activity in the brain resulting in temporary loss of consciousness, body convulsions changes in muscle tone, unusual movements and staring spells, all of which affect daily activities and the health of the affected individual (adults and children).

Seizure type and other factors could influence seizure duration. Most seizures last from 30 seconds to 2 minutes and do not cause lasting harm. However, there are also extreme forms of seizures that are prolonged and are considered as is a life-threatening medical and neurologic emergency.

Seizures can have many causes, including medicines, high fevers, head injuries and certain diseases. People who have recurring seizures due to a brain disorder have epilepsy.

The International League Against Epilepsy (ILAE) defines the following:

"Epileptic Disorder"—a chronic neurological condition characterized by recurrent epileptic seizures.

"Epilepsies"—those conditions involving chronic recurrent epileptic seizures that can be considered epileptic disorders.

"Epileptic seizure"—Manifestation(s) of epileptic (excessive and/or hypersynchronous), usually self-limited activity of neurons in the brain.

At least two unprovoked seizures are required for the diagnosis of epilepsy. This definition stress that the patient had the potential for more seizures and excludes seizures due to exogenous factors such as drug withdrawal.

Seizures are divided into categories based on the general behavior, symptoms and brain activity. There are several different types of seizures that fall under the following categories:

(1) Partial (seizures beginning locally)—A seizure whose initial semiology indicates, or is consistent with, initial activation of only part of one cerebral hemisphere.

(2) Generalized (bilaterally symmetric, without localized onset)—A seizure whose initial semiology indicates, or is consistent with, more than minimal involvement of both cerebral hemispheres. Generalized seizures may be subdivided to convulsive or non-convulsive seizures.

(3) Unclassified seizures—This category listed in the ILAE's Classification of Epileptic Seizures include all seizures that defy classification due to incomplete data. An example is seizure in infancy, which may involve chewing, swimming movements, eye movements and have not yet been subtyped.

Current treatments for seizure disorders include antiepileptic drugs (AED). However, such treatments can result in unwanted side-effects and may not treat the underlying cause of the seizure disorder.

In light of the emerging functional foods category in the area of dietary lipids, many health benefits have been attributed to the consumption of certain fatty acids. For example, it has been reported in many research studies that polyunsaturated fatty acids (PUFA) of the type omega-3 have several health benefits on cardiovascular disease (CVD), immune disorders, inflammation, renal disorders, allergies, diabetes, cancer and brain development and function. These types of fatty acids are naturally occurring mainly in fish, algae, and other marine products.

The professional literature emphasizes the importance of an adequate diet containing omega-3 fatty acids. Two very important omega-3 PUFA are Docosahexaenoic acid (DHA) and Eicosapentanoic acid (EPA) which modulate both metabolic and immune processes and confer health benefits in areas of CVD and brain development and health.

In addition to enhancing cardiovascular health, EPA and DHA have been shown to beneficially affect mood disorders, schizophrenia, major depressive disorder, anxiety, sleep disturbance, libido, suicidality, Perinatal Depression, Bipolar Disorder, attention-deficit hyperactive disorder (ADHD), obsessive-compulsive disorder (OCD) and Tourette.

DHA has been also suggested as a possible therapy to epilepsy due to its high safety profile. In vitro cell culture studies have demonstrated that unesterified DHA increases the threshold of action potential and reduces neuronal excitability in hippocampal slices.

A recent study by Trepanier, et al., demonstrated that unesterified omega-3 specifically DHA has anticonvulsant properties when administrated subcutaneous. Unesterified DHA increased seizure latencies in the maximal pentylenetetrazole (PTZ) seizure test. The researches demonstrated in male wistar rats that the optimal dose of unesterified DHA that increases seizure latencies is 400 mg/kg (Human Equivalent Dosage-3819 mg). Administration of 300 mg/kg EPA (Human Equivalent Dosage-2918 mg) together with Valproate, a known drug for the treatment of epilepsy with severe adverse events reveled alleviation of some of the adverse events as hepatotoxicity. Lower dose of EPA did not reveal the same effect.

In summary, in pre-clinical models it was suggested that high dosages of omega-3 fatty acids, may be beneficial for the treatment of epilepsy i.e. reducing the adverse event of anti-epileptic drugs or regulating seizure latencies.

Other lipid components which are presumed to be beneficial in a wide array of conditions are phospholipids. Phospholipids are key components of the lipid bilayer of cells, and are involved in cell metabolism and signaling. The hydroxyl groups of the glycerol backbone of phospholipids are substituted by a hydrophilic phosphate head and hydrophobic tail composed of non-polar fatty acids. Phospholipids may be subdivided into distinct classes, based on the nature of the polar head group such as for example: phosphatidylcholine (also known as PC or lecithin), phosphatidylethanolamine (PE), and phosphatidylserine (PS). In addition to serving as a primary component of cellular membranes and binding sites for intracellular and intercellular proteins, some phospholipids, such as phosphatidylinositols and phosphatidic acids are either precursors of, or are themselves, membrane-derived second messengers. Studies have shown that PS and PC enhance neuronal membrane function and improve memory skills. PS was found to have a beneficial effect in ADHD, depression, and chronic stress. In addition, PC was found to reduce emotional symptoms of premenstrual syndrome.

Apparently, the origin of the phospholipids and their fatty acid content influence their activity. For example, the biofunctionality of soybean PS in the improvement of cognitive function has been shown to be different from that of other types of PS [WO 2005/037848]. In addition, it was demonstrated that different ratios of specific fatty acids conjugated to PS can influence the efficacy of the PS in improving cognitive functions in elderly subjects with impaired cognitive performance [WO 2009/156991].

It is thus beneficial to apply the appropriate type of PS preparation for the specific indication.

SUMMARY OF THE INVENTION

The present invention discloses a preparation comprising a mixture of serine glycerophospholipids (PS) and a method for treatment and/or prevention of seizures (e.g. epileptic seizures). Optionally and preferably the PS mixture comprises Eicosapentaenoic acid (EPA) attached to the PS and Docosahexaenoic acid (DHA) attached to the PS.

Preferably, the ratio between (a) the percentage of EPA attached to the PS with respect to all fatty acids attached to the PS and (b) the percentage of DHA attached to the PS with respect to all fatty acids attached to the PS ((a)/(b)) is from about 0.2 to about 5 or 0.4 to about 5, more preferably, the ratio is above 1, even more preferably the ratio is from about 1 to about 4, or from about 1.1 to about 3, and most preferably from about 1.4 to about 3.

Preferably the percentage (w/w) of PS present in the preparation is greater than 10%, 20% or 30%, more preferably greater than 35% or 40%, even more preferably greater than 45% or 50%, and most preferably greater than 55%. Preferably, the percentage (w/w) of PS relative to the total phospholipids in the preparation is greater than 20%, 30% or 35%, more preferably 40% or 45%, more preferably greater than 50% or 55%, even more preferably greater than 60% and most preferable greater than 65%. Preferably, the preparation further comprises phosphatidic acid and lysophosphatidic acid and the ratio by weight of the PS in the preparation relative to the total weight of phosphatidic acid and lysophosphatidic acid in the preparation is greater than 1:1 and lower than 10:1, more preferably greater than 1.5:1 and lower than 8:1, even more preferably greater than 2:1 and lower than 5:1, and most preferably greater than 2.5:1 and lower than 4:1.

Preferably, the percentage of each of the following fatty acids: Eicosapentaenoic acid (EPA), Palmitic acid, Docosahexanoic acid (DHA), Oleic acid and Linoleic acid attached to the PS in the preparation relative to the total fatty acids content attached to the PS in the preparation is such that the percentage of EPA is greater than or equal to the percentage of Palmitic acid, the percentage of Palmitic acid is greater than the percentage of DHA, the percentage of DHA is greater than the percentage of Oleic acid, and the percentage of Oleic acid is greater than the percentage of Linoleic acid.

Preferably, the percentage of EPA attached to the PS in the preparation relative to the total fatty acids content attached to the PS in the preparation is greater than 18% and lower than 45%, preferably greater than 22% and lower than 40%, more preferably greater than 26% and lower than 36%, and most preferably greater than 27% and lower than 34%. Preferably, the percentage of Palmitic acid attached to the PS in the preparation relative to the total fatty acids content attached to the PS in the preparation is greater than 14% and lower than 42%, preferably greater than 18% and lower than 40%, more preferably greater than 20% and lower than 30%, and most preferably greater than 21% and lower than 26%. Preferably, the percentage of DHA attached to the PS in the preparation relative to the total fatty acids content attached to the PS in the preparation is greater than 6% and lower than 25%, preferably greater than 8% and lower than 22%, more preferably greater than 11% and lower than 20%, and most preferably greater than 12% and lower than 17%. Preferably, the percentage of Oleic acid attached to the PS in the preparation relative to the total fatty acids content attached to the PS in the preparation is greater than 1% and lower than 15%, preferably greater than 2% and lower than 13%, more preferably greater than 4% and lower than 11%, and most preferably greater than 5% and lower than 8%. Preferably, the percentage of Linoleic acid attached to the PS in the preparation relative to the total fatty acids content attached to the PS in the preparation is greater than 0.1% and lower than 6%, preferably greater than 0.5% and lower than 4%, more preferably greater than 1% and lower than 3%, and most preferably greater than 1.5% and lower than 2%.

The present invention also provides a preparation further comprises a percentage (w/w) of phosphatidylcholine (PC). Preferably the percentage (w/w) of PC is lower than 10% with respect to the preparation. Preferably, the percentage of PC with respect to the preparation is greater than 0.01% and lower than 8%, more preferably greater than 0.05% and lower than 6%, even more preferably greater than 0.1% and lower than 4%, and most preferably greater than 1% and lower than 3.5%.

The present invention provides a method for treatment and/or prevention of seizures by providing a therapeutically effective amount of any of the above mentioned PS preparations to a subject. More preferably, the therapeutically effective amount is provided as a daily dose.

Preferably, the method relates to treatment and/or prevention of seizures in subjects suffering epilepsy. More preferably to treatment and/or prevention of seizures in subjects suffering from complex partial epilepsy, generalized convulsive epilepsy and/or generalized non-convulsive epilepsy.

The present invention also provides a method for treatment and/or prevention of seizures by providing a therapeutically effective amount of any of the above mentioned PS preparations together with a therapeutically effective amount of AED to a subject. More preferably, the therapeutically effective amount is provided as a daily dose. Most preferably, the PS preparation according to the invention is provided with the AED together in the delivery unit.

Preferably the AED are selected from the group comprising: Valproic acid (e.g Depakote), Felbamate (e.g. Felbatol), phenobarbital and other barbiturates (e.g. primidone), Zonisamide, Clobazam, Trileptal (Oxcarbazepine) and any combination thereof.

DETAILED DESCRIPTION OF THE INVENTION

In the first aspect, the present invention discloses a preparation comprising a mixture of serine glycerophospholipids (PS) and a method for treatment and/or prevention of seizures (e.g. epileptic seizures). Optionally and preferably the PS mixture comprises Eicosapentaenoic acid (EPA) attached to the PS and Docosahexaenoic acid (DHA) attached to the PS.

Preferably, the ratio between (a) the percentage of EPA attached to the PS with respect to all fatty acids attached to the PS and (b) the percentage of DHA attached to the PS with respect to all fatty acids attached to the PS ((a)/(b)) is from about 0.2 to about 5 or 0.4 to about 5, more preferably, the ratio is above 1, even more preferably the ratio is from about 1 to about 4, or from about 1.1 to about 3, and most preferably from about 1.4 to about 3.

Preferably the percentage (w/w) of PS present in the preparation is greater than 10%, 20% or 30%, more preferably greater than 35% or 40%, even more preferably greater than 45% or 50%, and most preferably greater than 55%. Preferably, the percentage (w/w) of PS relative to the total phospholipids in the preparation is greater than 20%, 30%, or 35%, more preferably 40% or 45%, more preferably greater than 50% or 55%, even more preferably greater than 60% and most preferable greater than 65%. Preferably, the preparation further comprises phosphatidic acid and lysophosphatidic acid and the ratio by weight of the PS in the preparation relative to the total weight of phosphatidic acid and lysophosphatidic acid in the preparation is greater than 1:1 and lower than 10:1, more preferably greater than 1.5:1 and lower than 8:1, even more preferably greater than 2:1 and lower than 5:1, and most preferably greater than 2.5:1 and lower than 4:1.

Preferably, the percentage of each of the following fatty acids: Eicosapentaenoic acid (EPA), Palmitic acid, Docosahexanoic acid (DHA), Oleic acid and Linoleic acid attached to the PS in the preparation relative to the total fatty acids content attached to the PS in the preparation is such that the percentage of EPA is greater than or equal to the percentage of Palmitic acid, the percentage of Palmitic acid is greater than the percentage of DHA, the percentage of DHA is greater than the percentage of Oleic acid, and the percentage of Oleic acid is greater than the percentage of Linoleic acid.

Preferably, the percentage of EPA attached to the PS in the preparation relative to the total fatty acids content attached to the PS in the preparation is greater than 18% and lower than 45%, preferably greater than 22% and lower than 40%, more preferably greater than 26% and lower than 36%, and most preferably greater than 27% and lower than 34%. Preferably, the percentage of Palmitic acid attached to the PS in the preparation relative to the total fatty acids content attached to the PS in the preparation is greater than 14% and lower than 42%, preferably greater than 18% and lower than 40%, more preferably greater than 20% and lower than 30%, and most preferably greater than 21% and lower than 26%. Preferably, the percentage of DHA attached to the PS in the preparation relative to the total fatty acids content attached to the PS in the preparation is greater than 6% and lower than 25%, preferably greater than 8% and lower than 22%, more preferably greater than 11% and lower than 20%, and most preferably greater than 12% and lower than 17%. Preferably, the percentage of Oleic acid attached to the PS in the preparation relative to the total fatty acids content attached to the PS in the preparation is greater than 1% and lower than 15%, preferably greater than 2% and lower than 13%, more preferably greater than 4% and lower than 11%, and most preferably greater than 5% and lower than 8%. Preferably, the percentage of Linoleic acid attached to the PS in the preparation relative to the total fatty acids content attached to the PS in the preparation is greater than 0.1% and lower than 6%, preferably greater than 0.5% and lower than 4%, more preferably greater than 1% and lower than 3%, and most preferably greater than 1.5% and lower than 2%.

The present invention also provides a preparation further comprises a percentage (w/w) of phosphatidylcholine (PC). Preferably the percentage (w/w) of PC is lower than 10% with respect to the preparation. Preferably, the percentage of PC with respect to the preparation is greater than 0.01% and lower than 8%, more preferably greater than 0.05% and lower than 6%, even more preferably greater than 0.1% and lower than 4%, and most preferably greater than 1% and lower than 3.5%.

The present invention provides a method for treatment and/or prevention of seizures by providing a therapeutically effective amount of any of the above mentioned PS preparations to a subject. More preferably, the therapeutically effective amount is provided as a daily dose.

Preferably, the method relates to treatment and/or prevention of seizures in subjects suffering epilepsy. More preferably to treatment and/or prevention of seizures in subjects suffering from complex partial epilepsy, generalized convulsive epilepsy and/or generalized non-convulsive epilepsy.

The present invention also provides a method for treatment and/or prevention of seizures by providing a therapeutically effective amount of any of the above mentioned PS preparations together with a therapeutically effective amount of AED to a subject. More preferably, the therapeutically effective amount is provided as a daily dose. Most preferably, the PS preparation according to the invention is provided with the AED together in the delivery unit.

Preferably the AED are selected from the group comprising: Valproic acid (e.g Depakote), Felbamate (e.g. Felbatol), phenobarbital and other barbiturates (e.g. primidone), Zonisamide, Clobazam, Trileptal (Oxcarbazepine) and any combination thereof.

As used herein treatment of seizures, epileptic seizures or seizure disorder includes one or more of reducing the frequency of seizures, ameliorating the severity of the seizures or the overall disorder, treating seizures or the overall disorder, curing the seizures or the overall disorder, reducing the AED dose necessary for stabilizing the patient, reducing the degree of side effects that arise from AED treatment, achieving a reduction in the number or severity of the seizures, reducing the frequency of hospitalization required to treat the seizures, reducing the duration of hospitalization as a result of the seizures, improving the quality of life of the patient experiencing the seizures, or reducing the severity of comorbidities that accompany the seizures or overall disorder such as attention deficit hyperactivity disorder or cognitive impermanent or allowing the proper development of infants brain.

As used herein the term "improving the seizure disorder", or "improving seizures" is described as reducing the frequency of seizures and/or reducing the severity of the seizures (stabilization of the seizure state), and/or maintaining a seizure free state in a subject, and/or ameliorating undesired symptoms associated with a disease, disorder, and/or pathological condition, and/or prevention of the manifestation of symptoms before they occur, and/or slowing down irreversible damage caused by the seizures, and/or reducing severity of a disease or disorder, and/or curing a disease or disorder, and/or preventing a disease or disorder from occurring altogether (for example in an individual genetically and/or phenotypically prone to the disease) or a combination of any of the above. For example, in a subject suffering from a seizure or overall disorder, improvement is expected by use of the lipid preparation of the invention.

By "seizures", it is meant any non-chronic or chronic seizure, inclusive of, seizures resulting from epilepsy, epilepsy disorder, audiogenic seizure disorder, epilepsy syndromes and related conditions. Seizures resulting from high fever, abnormal blood levels of sodium or glucose, drug abuse, certain medications, high blood pressure, phenylketonuria and uremia, as well as acute seizure disorders such as those caused by a brain tumor and/or brain injury, which may in turn become chronic seizure disorders. The term "epileptic disorder" or "epilepsy" refers to a chronic neurological condition characterized by recurrent epileptic seizures. The term "Epilepsies" refers to those conditions involving chronic recurrent epileptic seizures that can be considered epileptic disorders. The term epileptic seizure should be understood to encompass any state of seizure whether apart of the epileptic disorder or as a result of another syndrome or related condition.

Non-limiting examples for types of epileptic seizures are partial seizures (e.g. Simple partial seizures, Complex partial seizures, partial seizures evolving to secondarily generalized seizures, partial elementary seizures, partial (psychomotor) complex seizures or temporal lobe epilepsy), generalized seizures (convulsive and nonconvulsive; e.g. Absence seizures, Atypical absence seizures, Myoclonic seizures, Clonic seizures, Tonic seizures, Tonic-clonic seizures, Atonic seizures (astatic), secondary generalized seizures and other chronic unclassifiable seizures.

Non-limiting examples for Epilepsy syndromes and related conditions are Benign familial neonatal seizures, Early myoclonic encephalopathy, Ohtahara syndrome, Migrating partial seizures of infancy, West syndrome, Benign myoclonic epilepsy in infancy, Benign familial infantile seizures, Benign infantile seizures (nonfamilial), Dravet syndrome, Hemiconvulsion-hemiplegia syndrome, a Myoclonic status in nonprogressive encephalopathies, Benign childhood epilepsy with centrotemporal spikes, Early-onset benign childhood occipital epilepsy (Panayiotopoulos type), Late-onset childhood occipital epilepsy (Gastaut type), Epilepsy with myoclonic absences, Epilepsy with myoclonic-astatic seizures, Lennox-Gastaut syndrome, Landau-Kleffner syndrome (LKS), Epilepsy with continuous spike-and-waves during slow-wave sleep (other than LKS), Childhood absence epilepsy, Progressive myoclonus epilepsies, Idiopathic generalized epilepsies with variable phenotypes, Juvenile absence epilepsy, Juvenile myoclonic epilepsy, Epilepsy with generalized tonic-clonic seizures only, Reflex epilepsies, Idiopathic photosensitive occipital lobe epilepsy, Other visual sensitive epilepsies, Primary reading epilepsy, Startle epilepsy, Autosomal dominant nocturnal frontal lobe epilepsy, Familial temporal lobe epilepsies, a Generalized epilepsies with febrile seizures plus, a Familial focal epilepsy with variable foci, Symptomatic (or probably symptomatic) focal epilepsies, Limbic epilepsies, Mesial temporal lobe epilepsy with hippocampal sclerosis, Mesial temporal lobe epilepsy defined by specific etiologies, Other types defined by location and etiology, Neocortical epilepsies, Rasmussen syndrome, Other types defined by location and etiology, Conditions with epileptic seizures that do not require a diagnosis of epilepsy, Benign neonatal seizures, Febrile seizures, Reflex seizures, Alcohol-withdrawal seizures, Drug or other chemically induced seizures, Immediate and early post-traumatic seizures, Single seizures or isolated clusters of seizures, Rarely repeated seizures (oligoepilepsy).

According to at least some embodiments, the PS preparation of the invention further comprises an anti-seizure drug, such as an AED According to at least some embodiments, the method may optionally comprise administering the AED and the phospholipid composition as described herein together or separately.

Non-limiting examples of drugs indicated for the treatment and/or prevention of seizures, seizure disorders, epileptic seizures or epilepsy include, but are not limited to, Sodium channel blockers (such as Phenytoin, Carbamazepine, Fosphenytoin, Zonisamide, lamotrigine, Oxcarbazepine, Eslicarbazepine, Lacosamide, Vimpat Valporate, Rufinamide), Calcium channel blockers (such as Ethosuximide, Zarontin), GABA Receptor Agonists (such as Clobazam, Clonazepam, Phenobarbital, Barbiturates, and Primidone, Benzodiaz, Progabide, Onfi), GABA Reuptake Inhibitors (such as Tiagabine), GABA Transaminase Inhibitors (such as Vigabatrin), AEDs with Potential GABA Mechanism of Action (such as Gabapentin, Pregabalin, Valproate, Depakote), Glutamate Blockers (such as Felbamate, Felbatol Topiramate and Perampanel), AEDs with Other Mechanisms of Action (such as Levetiracetam), Neuronal Potassium Channel Openers such as (Ezogabine), histone deacetylase inhibitor (such as Valporate), Carbonic anhydrase inhibitors (such as Acetazolamide, Topiramate, zonisamide), Sex hormones (such as Progesterone), Synaptic vesicle protein 2A (SV2A) binding agents such as (such as Levetiracetam).

The preparation of the invention and/or method according to at least some embodiments relates to reducing the frequency of seizures, ameliorating the severity of the seizures or the overall disorder, treating the seizures or the overall disorder, curing the seizures or the overall disorder, reducing the AED dose necessary for stabilizing the patient, reducing the degree of side effects that arise from AED treatment, achieving a reduction in the number or severity of the seizures, reducing the frequency of hospitalization required to treat the seizures, reducing the duration of hospitalization as a result of the seizures, improving the quality of life of the patient experiencing the seizures, or reducing the severity of comorbidities that accompany the seizures or overall disorder such as attention deficit hyperactivity disorder or cognitive impairment or allowing the proper development of infants brain.

The method according to at least some embodiments relates to reducing the frequency of seizures, ameliorating the severity of the seizures or the overall disorder, treating the seizures or the overall disorder, curing the seizures or the overall disorder, reducing the AED dose necessary for stabilizing the patient, reducing the degree of side effects that arise from AED treatment, achieving a reduction in the number or severity of the seizures, reducing the frequency of hospitalization required to treat the seizures, reducing the duration of hospitalization as a result of the seizures, improving the quality of life of the patient experiencing the seizures, or reducing the severity of comorbidities that accompany the seizures or overall disorder such as attention deficit hyperactivity disorder or cognitive impairment or allowing the proper development of infants brain, by administering to a subject in need thereof a PS preparation according to at least some embodiments of the invention.

Optionally, the specific weight per weight percentage of PS present in the preparation is about 10%-90%, preferably 10%-70%, preferably 20%-60%, more preferably 30%-60% and most preferably 40%-55%.

According to at least some embodiments, a daily dose of the preparation of the invention as described herein optionally provides 75-600 mg PS to the subject, preferably 75-450 mg PS, more preferably 75-300 mg PS, more preferably 75-225 and most preferably 75-150 mg PS. The daily dose may optionally be divided to a plurality of doses each day or alternatively may optionally be delivered as a single bolus each day.

According to at least some embodiments, a daily dose of the preparation of the invention as described herein optionally provides 20-172 mg EPA to the subject, preferably 21.5-129 mg EPA, more preferably 21.5-86 mg EPA and most preferably 21.5-43 mg EPA. The daily dose may optionally be divided to a plurality of doses each day or alternatively may optionally be delivered as a single bolus each day.

According to at least some embodiments, a daily dose of the preparation of the invention as described herein optionally provides 8-68 mg DHA to the subject, preferably 8-51 mg DHA, more preferably 8-34 mg DHA and most preferably 8-17 mg DHA. The daily dose may optionally be divided to a plurality of doses each day or alternatively may optionally be delivered as a single bolus each day.

According to at least some embodiments, the present invention encompasses a nutritional, pharmaceutical or nutraceutical composition, or a functional food or a medical food, as well as embodiments relating to the manufacture of such compositions and foods thereof.

In a further aspect the invention provides a preparation of the invention, for use in a nutritional, pharmaceutical or nutraceutical composition or a functional food or a medical food.

In yet a further aspect the invention provides a nutritional, pharmaceutical or nutraceutical composition or a functional food or a medical food comprising a preparation of the invention.

In another embodiment of the present invention the preparation is provided as a pharmaceutical composition in admixture with pharmaceutically acceptable auxiliaries, and optionally other therapeutic agents. The auxiliaries must be "acceptable" in the sense of being compatible with the other ingredients of the composition and not deleterious to the recipients thereof.

According to another embodiment, the compositions are in a dosage delivery form selected according to the route of administration.

Suitable routes of administration for the compositions of the subject invention are oral, buccal, sublingual administration, administration via a feeding tube, topical, transdermal, or parenteral (including subcutaneous, intramuscular, intravenous and intradermal) administration. In an embodiment, the compounds are administered orally.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated.

According to another embodiment, the present invention can be administered in the form of capsules, tablets, pills, gummies, fluid oils, powders, granules, waxes, pastes, aqueous emulsions, and any other form that will enable its use in the target applications.

The daily dose according to at least some embodiments of the present invention, when administered as capsules, tablets, syrups, gummys, and other known delivery systems, optionally comprises one, two, three, four, five, six, seven or eight delivery units per day.

A nutritional composition as described herein can be any nutritional composition including, but not limited to, human milk fat substitute, infant formula, dairy product, milk powder, drinks, ice-cream, biscuit, soy product, bakery, pastry and bread, sauce, soup, prepared food, frozen food, condiment, confectionary, oils and fat, margarine, spread, filling, cereal, instant product, infant food, toddler food, bar, snack, candy and chocolate product.

A functional food as used herein can be any functional food, including, but not limited to, dairy product, ice-cream, biscuit, soy product, bakery, pastry, cakes and bread, instant product, sauce, soup, prepared food, frozen food, condiment, confectionary, oils and fat, margarine, spread, filling, cereal, instant product, drinks and shake, infant food, bar, snack, candy and chocolate product.

A nutraceutical composition as used herein can be any nutraceutical, which can be any substance that may be considered a food or part of a food and provides medical or health benefits, including the prevention and treatment of diseases or disorders. Such nutraceutical compositions include, but are not limited to, a food additive, a food supplement, phospholipid mixtures, Phosphatidylserine from other sources, a dietary supplement, genetically engineered foods such as for example vegetables, herbal products, and processed foods such as cereals, soups and beverages and stimulant functional food, medical food and pharmafood. Dietary supplements may be delivered in the form of soft gel capsules, tablets, syrups, gummy candies, and other known dietary supplement delivery systems.

A medical food as used herein is specially formulated and intended for the dietary management of a disease that has distinctive nutritional needs that cannot be met by normal diet alone.

The exact dose and regimen of administration of the composition will necessarily be dependent upon the therapeutic effect to be achieved (e.g. reducing the frequency of and/or severity seizures and/or ameliorating the severity of the seizure disorder) and may vary with the particular formula, the route of administration, and the age and condition of the individual subject to whom the composition is to be administered.

The present invention, in at least some embodiments, thus also provides pharmaceutical compositions of the invention in admixture with (pharmaceutically) acceptable auxiliaries, and optionally other therapeutic agents. The auxiliaries must be "acceptable" in the sense of being compatible with the other ingredients of the composition and not deleterious to the recipients thereof.

In an embodiment, a pharmaceutical composition of the invention further comprises at least one pharmaceutically active agent.

The pharmaceutical and nutraceutical compositions may be prepared by any method well known in the art of pharmacy. Such methods include the step of bringing in association the ingredients with any auxiliary agent. The auxiliary agent(s), also named accessory ingredient(s), include those conventional in the art, such as carriers, fillers, binders, diluents, dessicants, disintegrants, lubricants, colorants, flavoring agents, anti-oxidants, and wetting agents.

The pharmaceutical and nutraceutical compositions of the invention may further comprise edible fibers, aroma, taste ingredients, and ingredients that control physical and organoleptic properties.

The compositions may be presented in unit-dose or multi-dose containers, for example sealed vials and ampoules, and may be stored in a freeze-dried (lyophilised) condition requiring only the addition of sterile liquid carrier, for example water, prior to use.

It should be noted that the preparation of the invention may also comprise other phospholipids, such as phosphatidylcholine (PC), phosphatidylethanolamine (PE), phosphatidyl-inositol (PI), phosphatidylglycerol (PG) and phosphatidic acid (PA), to which fatty acid acyls are covalently attached (bonded) at either or both of the sn-1 or sn-2 positions of the glycerol moiety of the phospholipid. The fatty acid conjugation profile of any of the above-noted polar lipids may be the same as, or different from, the fatty acid conjugation profile of PS, as disclosed herein.

The terms "glycerophosphohpid" and "phospholipids" are used herein interchangeably and should be understood to encompass a lipid of the general formula:

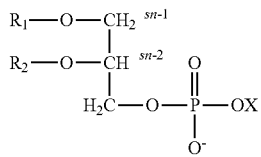

Wherein X represents a moiety selected from serine, choline, ethanolamine, inositol, glycerol and hydrogen, and R1 and R2, which may be identical or different, independently represent hydrogen or an acyl group, wherein said acyl group is selected from saturated, mono-unsaturated or poly-unsaturated acyl groups (PUFA). The sn-1 and sn-2 positions as used herein and as indicated in above formula, refer to the respective carbon atoms on the glycerol backbone wherein R1 and R2, are hydrogen or acyl groups substituted on the corresponding position.

The term "lysophosphatidic acid" is used herein when X represents hydrogen and one of R1 or R2 is Hydrogen as well.

As described herein, the terms "substituted," "conjugated,", and "attached" are used interchangeably and should be understood to encompass a fatty acid acyl covalently attached to the glycerophospholipid backbone of a phospholipid of the invention. As noted above, the fatty acid may be attached to the sn-1 and/or sn-2 positions.

As used herein, the term "fatty acid" should be understood to encompass a carboxylic acid with a long unbranched aliphatic tail (chain), which is either saturated or unsaturated having one unsaturated bond (mono-unsaturated fatty acids) or two or more unsaturated bonds (poly-unsaturated fatty acids). When referring to a "fatty acid acyl" it should be understood to encompass an —C(=O)—R radical wherein R is a long unbranched aliphatic tail, which is either saturated or unsaturated having one unsaturated bond (mono-unsaturated fatty acids) or two or more unsaturated bonds (poly-unsaturated fatty acids).

As used herein, the term ω, Omega, n-X (X denotes a number), are interchangeably used and should be understood to denote the carbon atom furthest from the carboxyl group of a fatty acid.

Non-limiting examples of saturated fatty acids include: Butyric acid (Butanoic acid, C4:0), Caproicacid (Hexanoic acid, C6:0), Caprylic acid (Octanoic acid, C8:0), Capric acid (Decanoic acid, C10:0), Lauric acid (Dodecanoic acid, C12:0), Myristic acid (Tetradecanoic acid, C14:0), Palmitic acid (Hexadecanoic acid, C16:0), Stearic acid (Octadecanoic acid, C18:0), Arachidic acid (Eicosanoic acid, C20:0), Behenic acid (Docosanoic acid C22:0).

Non-limiting examples of unsaturated fatty acids include: Myristoleic acid (C14:1, ω-5), Palmitoleic acid (C16:1, ω-7), Oleic acid (C18:1, ω-9), Linoleic acid (C18:2, ω-6), Linolenic acid (C18:3) [Alpha-linolenic acid (C18:3, ω-3), Gamma-linolenic acid (C18:3, ω-6)], Eicosenoic acid (C20:1, ω-9), Arachidonic acid (C20:4, ω-6), Eicosapentaenoic acid (C20:5, ω-3), Erucic acid (C22:1, ω-9), Docosapentanoic acid (C22:5, ω-3) and Docosahexaenoic acid (C22:6, ω-3), Nervonic acid (C24:1, ω-9).

The term a "[fatty acid] conjugated to PS", should be understood to encompass a PS wherein a fatty acid acyl is conjugated at position sn-1 and/or position sn-2 of the phospholipid backbone (through the glycerol oxygen atom). In one embodiment a fatty acid is conjugated at position sn-1, and position sn-2 is either unsubstituted (e.g. having a hydrogen atom on the glycerol oxygen) or substituted with an acyl group selected from saturated, mono-unsaturated and polyunsaturated fatty acids, which may be the same or different from the substitution on position sn-1. In another embodiment a fatty acid is conjugated at position sn-2 and position sn-1 is either unsubstituted (e.g. having a hydrogen atom on the glycerol oxygen) or substituted with an acyl group selected from saturated, mono-unsaturated and polyunsaturated fatty acids, which may be the same or different from the substitution on position sn-2.

The term phosphatidylserine is often also referred to in the literature as serine glycerophospholipid, phosphatidyl serine, and PS.

The term phosphatidylcholine is often also referred to in the literature as Choline glycerophospholipid, phosphatidyl choline, and PC.

A preparation of the invention as described herein typically comprises a mixture of two or more serine glycerophospholipid conjugates of the invention, having fatty acid conjugation patterns as disclosed herein.

A preparation of the invention may also be administered in conjunction with other compounds, including, but not limited to folic acid, vitamins, minerals, amino acids, nucleotides, antioxidants and so forth.

It will be appreciated that a composition (whether pharmaceutical, nutraceutical, nutritional, medical food, etc.) or product (e.g. functional food) of the invention may be combined with other treatment methods known in the art (i.e., combination therapy). Thus, treatment of seizures (e.g. epileptic seizures) or epilepsy or epileptic disorders using a composition or product of the invention may optionally be combined with conventional drugs for the treatment of epileptic seizure or disorders.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising," will be understood to imply the inclusion of a stated integer or step or group of integers or steps but not the exclusion of any other integer or step or group of integers or steps.

A preparation as described herein may be optionally prepared through enzymatic, chemical or molecular biology methods, but preferably comprises phospholipids which are not derived from a mammalian source. Briefly, PS can be enriched with EPA and/or DHA by enzymatic processes, e.g. enrichment of a natural phospholipid/lecithin with EPA and/or DHA by enzymatic transesterification/esterification followed by transformation of the head group to serine (using PLD enzymes) to obtain EPA and/or DHA conjugated to PS.

Another enzymatic pathway is to obtain a phospholipid source which is naturally rich in EPA and/or DHA, such as marine-derived lecithin (e.g. krill, fish, algae, squid) or eggs phospholipids, and transform their head groups to serine. It is to be noted that the fatty acid content of the PS obtained by this method has EPA and/or DHA content which is predetermined by the source of choice (fish, krill, algae, soy etc.).

Such methods of preparation have been described in WO 2005/038037.

Alternatively, the PS preparation according to at least some embodiments of the present invention can be prepared by GMO (genetically modified organisms)/biotechnology methods, for example, providing phospholipids-producing organisms with EPA and/or DHA to obtain phospholipids enriched with EPA and/or DHA. It may be preferred to use genetically engineered plants or microorganisms, to avoid use of animal sources.

Thus, a mixture of serine glycerophospholipid conjugates according to at least some embodiments of the present invention is preferably prepared from a natural, synthetic or semi-synthetic source or any combinations thereof. In an embodiment of the present invention, said natural source is derived from any one of plant (such as for example soy and algae), non-mammalian animal (such as for example krill, fish (such as for example Herring and blue Whiting)), or microorganism (such as for example bacteria) source or any combinations thereof.

In yet a further embodiment, the production of said lipid preparation involves an enzymatic catalysis.

Quantification of Phospholipids by 31P-NMR spectroscopy using the internal standard method.

Purpose: This method is used to determine the phospholipid content by weight in the preparation.

Instruments: Bruker Avance III 600 MHz with automatic sample changer and cQNP probe head. Bruker Avance 300 MHz with automatic sample changer and BBI probe head. For the quantification of phospholipids in the preparation of the invention (powder form) approximately 300 mg of the test substance and 20 mg of internal standard TPP (triphenylphosphate) is dissolved in 1.5 ml CDCl3, 3 ml methanol and 3 ml aqueous Cs-EDTA solution (0.2 m, pH 7.5). After 15 minutes of shaking, the organic layer is separated by centrifugation and measured with 31P-NMR. The integrated signals of the test substance and of the internal standard TPP (triphenylphosphate) are used for calculation. The ratio of integrals corresponds to the molar ratio of the compared substances. For calculation software Microsoft Excel 14.0 is used.

Calculation:

$$MOL_{IS}[mMol] = \frac{W_{IS}[mg] * C_{IS}[\%]}{MW_{IS}[g/mol] * 100}$$ Equation 1

$$MOL_P[mMol] = \frac{I_P * H_{IS} * MOL_{IS}[mMol]}{I_{IS} * H_P}$$ Equation 2

$$weight\text{-}\%_P = \frac{MW_P[g/Mol] * MOL_P[mMol] * 100}{W_P[mg]}$$ Equation 3

Declaration of variables:

|  | test substance | internal standard |
|---|---|---|
| molecular weight | $MW_P$ (According to the MW table presented below) | $MW_{IS}$ |
| initial weight [mg] | $W_P$ | $W_{IS}$ |
| content [%-by weight] | weight-$\%_P$ | $C_{IS}$ |
| Mol [mMol] | $MOL_P$ | $MOL_{IS}$ |
| integral | $I_P$ | $I_{IS}$ |
| number of P-atoms | $H_P$ | $H_{IS}$ |

| Phospholipid | MW (g/mol) |
|---|---|
| Phosphatidylcholine (PC) | 812.0 |
| Lyso Phosphatidylcholine (LPC) | 534.5 |
| Phosphatidylinositol (PI) | 907.0 |
| Lyso Phosphatidylinositol (LPI) | 629.5 |
| Phosphatidylserine (PS) | 833.0 |
| Lyso Phosphatidylserine (LPS) | 555.5 |
| Phosphatidyl Ethanolamine (PE) | 770.0 |
| Lyso Phosphatidyl Ethanolamine (LPE) | 492.5 |
| Phosphatidic Acid (PA) | 746.0 |
| Lyso Phosphatidic Acid (LPA) | 468.5 |
| Acyl Phosphatidyl Ethanolamine (APE) | 1032.0 |
| Other | 812.0 |

Determination of Fatty Acid Percentage in Phospholipids

Purpose: This method is used to determine the percentage of each fatty acid attached to PS with respect to the total fatty acid content attached to PS.

Materials: Acetic acid glacial A.R., Methanol abs. A.R., Chloroform A.R., Acetone A.R., Hexane A.R., Toluene A.R., Di-isopropyl ether AR., Butylhydroxytoluene, Sigma Lot # W218405 or equivalent, Sodium Sulfate Anhydrous, Sigma, Lot #31481, or equivalent, Sodium methoxide 25% (w/w) in methanol, Sigma Cat #15625-6, or equivalent, Primuline, Sigma Cat #206865, or equivalent, GC reference standard, Nuchek Lot #566B, Phosphatidylcholine reference standard, Sigma Aldrich Lot Cat # P3556, or equivalent, Phosphatidylserine reference standard, Sigma Aldrich Lot Cat # P5660, or equivalent, TLC Plates 20×10, silica gel 60 F254 layer MERCK 1.05715, or equivalent.

Apparatus: Orbital shaker with temperature control, Analytical Balance, Pipettor 0.2-1 ml and 1-5 ml range, Volumetric pipette 10 ml class A,TLC tank, suitable for 20×10 TLC plates, Disposable capillaries 5 µl volume, GC systems suitable for use with capillary column, equipped with oven capable of maintaining temperature with +0.1 C. degree accuracy, FID detector, split mode injection unit with temperature controller, GC capillary column, G16 USP phase, length 30 m, I.D. 0.25 mm, film 0.25 µm, or similar.

Reagents and solutions preparation: Sodium Methoxide solution: Accurately weigh 54 g of Sodium methoxide 25% into a 500 ml volumetric flask. Dilute to volume with Methanol Abs. Store in a dark place, in a tightly closed glass container. Solution is stable for up to 3 months.

Chloroform:Methanol 95:5 solution: Mix 95 volumes of Chloroform with 5 volumes of Methanol. Store in a dark place, in a tightly closed glass container. Solution is stable for up to one year.

Developing solution: Mix Water, Methanol, Acetic acid, Acetone and Chloroform in the following volume ratio 5:10:15:20:50. Store in a dark place, in a tightly closed glass container. Solution is stable for up to one year.

Primuline solution: Accurately weight 10 mg of into a 100 ml volumetric flask. Add 60 ml Acetone and 40 ml water. Mix well. Store in a dark place, in a tightly closed glass container. Solution is stable for up to one year.

Antioxidant solution 1 mg/ml: Weighed 25±2 mg Butyl-hydroxytoluene into a 25 ml volumetric flask. Add Toluene to the Mark, mix well (This solution can be kept for 3 month at room temperature.). Antioxidant solution 0.05 mg/ml: Pipette 10 ml of the above solution into a 200 ml volumetric flask, add Toluene to the Mark, mix well. Store at 50° C. for up to 3 months. (This solution can be kept for 3 months at room temperature).

PS/PC mix standard solution: Add about 20 mg of Phosphatidylserine reference standard into a 2 ml volumetric flask, add about 20 mg of Phosphatidylcholine reference standard. Add a small amount of Chloroform:Methanol solution sufficient to dissolve the reference standards. Once dissolved fill up to volume with the same Chloroform:Methanol solution. Store in a tightly closed container at −20° C. Stable for up to 3 months.

System suitability solution: Empty an ampoule containing 100 mg of GC reference standard 566B into a 50 ml volumetric flask, add 0.05 mg/ml Antioxidant Solution 0.05 mg/ml to the Mark. Mix well. Store in tightly closed container at −20° C. Stable for up to 3 months.

Procedure: Sample solution preparation: Accurately weight 500 mg of the sample into a 20 ml vial with ground stopper. Add 10 ml Chloroform: Methanol solution and shake vigorously for 2-3 minutes.

Phospholipids purification: Perform test in duplicate. Perform blank determination by developing an unloaded plate (no sample applied to the plate). Sample silica from an area corresponding to the area of the sample followed by methylation as described above. Apply an even thin band of 120 µl sample solution on TLC plate, 1 cm above the plate bottom, leaving a 3 cm margin on each side. At one of the margins, apply PS/PC mix standard solution of approximately 5 µl, spot wise by means of a disposable capillary. Add 45 ml of di-isopropyl ether to the 20×10 mm Glass TLC chamber. Saturate the chamber for 15-20 minutes. Develop TLC plate up to about 90 mm mark. Dry the plate in fume hood under air at room temperature for about 10 minutes. Repeat the previous two steps once more using the same chamber. Add 45 ml of developing solution to the 20×10 mm Glass TLC chamber. Saturate the chamber for 15-20 minutes. Develop TLC plate up to about 80 mm mark. Dry the plate in fume hood under a current of air at room temperature for about 10 minutes. Spray the TLC plate evenly with Primuline solution and dry under a current of air at room temperature for about 10 minutes. Place the plate under UV lamp at 365 nm to observe the bands. Identify the corresponding bands using spots of PS mix reference standard and scrub the bands in-to a 20 ml glass vial with ground stopper.

Methylation: To the 20 ml vials containing scrubbed silica add 2 ml Toluene. Then add 4 ml of Sodium methoxide solution. Shake for 15 minutes at 50° C. Then add 200 µl of Acetic acid and 4 ml of purified water, shake vigorously for 1 minute. Add 2 ml of Hexane and shake vigorously for 30 seconds. Transfer only the upper organic layer to a 20 ml bottle. Again add 2 ml of Hexane and shake vigorously for 30 seconds. Transfer only the upper organic layer to the same 20 ml bottle. Combine organic phases and dry over 0.5 grams Sodium sulfate. Filter through a 0.2 micron filter. Evaporate hexane under a nitrogen stream, until a volume of about 0.5 ml is reached. Analyze the sample by Gas Chromatography.

Gas Chromatography Settings:

| Column | Capillary column, G16 USP phase, length 30 m, I.D. 0.25 mm, film 0.25 µm, or similar |
|---|---|
| Carrier gas | Helium |
| Equilibration time | 2 min |

| | Initial Temp | Initial Time | First Temp. rate | Final Temp. | Hold Time |
|---|---|---|---|---|---|
| Temperatures | 170° C. | 2 min | 1° C./min | 210° C. | 2 min |

| | | | Second Temp. rate | Final Temp. | Hold Time |
|---|---|---|---|---|---|
| | | | 30° C./min | 240° C. | 11 min |

| Injector temp. | 250° C. |
|---|---|
| Pressure | 21 psi |
| Split ratio | 25:1 |
| Helium flow | 1.5 ml/min (constant flow) |
| Total flow | 41.4 ml/min |
| Detector temp. | 270° C. |
| Hydrogen flow | 40 ml/min |
| Air flow | 400 ml/min |
| Injection volume | 1 µl |

Note:
Gas flow and temperature ramp may be adjusted to meet system suitability acceptance criteria.

Chromatography Injection Order: First inject Hexane and insure that there is no response in the relevant Retention time. Next, inject System Suitability solution. The acceptance criteria is as follows: the resolution (R) between the peaks due to methyl oleate (C18:1n9) and methyl cis-vaccinate (C:181n11)≥1.3.

$$\text{resolution } R = \frac{2(t2 - t1)}{1.7(W1 + W2)}$$

where, t1 and t2 are the retention times of the two components and W1 and W2 are the corresponding widths at half-height of the peaks.

Next, inject sample from blank TLC plate (TLC blank). If there are peaks observed in the TLC blank chromatogram (except the solvent peak), they must be subtracted from the chromatogram of the sample. Finally, inject Samples.

Calculation:

Calculate the area percentage of each fatty acid component in sample by the formula: % FA=AreaFA/AreaTot, where AreaFA is the area of the peak response obtained for each individual fatty acid methyl ester and AreaTot is the sum of the peak areas of all of the peaks, corresponding to fatty acids methyl esters. Report the results indicating two digits after decimal point. Relative standard deviation between the replicates should not exceed 5%.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Example 1: The Effect of the Preparation of the Invention on Seizure Frequency in Epilepsy Patients Study Design:

The effect of the preparation of the invention on seizure frequency was evaluated in 13 children and adults (7 females and 6 males), 5-21 years of age, who were diagnosed with epilepsy and treated with known AED, and who have been experiencing a recent seizure episode. All study patients received the preparation of the invention on top of their medication regime for at least 3 months.

Epilepsy type, concurrent AED and effect on the epileptic status were evaluated via electronic health record reviews and are described in Table 2, provided separately. Of the study patients, four received a single type of AED, two received two types of AED, five received three types of AEDs and two received four types of AEDs. Eight patients were diagnosed with complex partial epilepsy, two with generalized convulsive epilepsy and three with generalized non convulsive epilepsy.

Treatment:

All patients received a daily dose of 2 capsules a day, providing the preparation of the invention and comprising 150 mg of PS, 43 mg of EPA, and 17 mg of DHA (see additional information regarding the preparation compositions in Table 1 below.

TABLE 1 list of ingredients in one capsule (167 mg per capsule) containing the phospholipid preparation

| Parameter | Specification |
|---|---|
| Phophatidylserine | n.l.t. 75 mg/capsule |
| Phophatidylcholine | n.l.t. 0.0165 mg/capsule |

TABLE 1-continued list of ingredients in one capsule (167 mg per capsule) containing the phospholipid preparation

| Parameter | Specification |
|---|---|
| Phosphatidic acid | n.l.t. 13 mg/capsule |
| Lysophosphatidic acid | n.l.t. 2 mg/capsule |
| Total DHA | n.l.t. 8.5 mg/capsule |
| Total EPA | n.l.t. 21.5 mg/capsule |
| Total Palmitic acid | n.l.t. 16.5 mg/capsule |
| Total Oleic acid | n.l.t. 3.5 mg/capsule |
| Total Linoleic acid | n.l.t. 1 mg/capsule |
| Percentage (% w/w) of phosphatidylserine (PS) with respect to the preparation | 40-48% |
| Percentage (% w/w) of PS to total phospholipids in the preparation | 51-60% |
| Percentage (% w/w) of phosphatidylcholine (PC) with respect to the preparation | 0.05-3.2% |
| Ratio (w/w) of the PS to the sum of phosphatidic acid and lysophosphatidic acid | 2.5:1-4:1 |
| Percentage of EPA attached to the PS with respect to all fatty acids attached to the PS | 27-34% |
| Percentage of Palmitic acid attached to the PS with respect to all fatty acids attached to the PS | 21-26% |
| Percentage of DHA attached to the PS with respect to all fatty acids attached to the PS | 12-17% |
| Percentage of Oleic acid attached to the PS with respect to all fatty acids attached to the PS | 5-8% |
| Percentage of Linoleic acid attached to the PS with respect to all fatty acids attached to the PS | 1-2% |
| Ratio between (a) the percentage of EPA attached to the PS with respect to all fatty acids attached to the PS/(b) the percentage of DHA attached to the PS with respect to all fatty acids attached to the PS (a/b) | 1.4-3 |

Results:

The results are summarized in Table 2.

TABLE 2

The effect of PS preparation on seizures

| Subject No. | Age | Gender | Number of Anti epileptic drugs received | Epilepsy type | Concurrent AED | Effect on Drug dose | PS preparation effect at endpoint | Duration of PS preparation use |
|---|---|---|---|---|---|---|---|---|
| 1 | 19 | F | 3 | Complex Partial | Depakote | Decreased dose | Fewer and more mild seizures | 3.5 months |
|  |  |  |  |  | Onfi | No change |  |  |
|  |  |  |  |  | Felbatol | No change |  |  |
| 2 | 7 | F | 1 | Generalized Non-convulsive | Depakote | No change | stable during the 11.5 months of treatment - no additional seizures | 11.5 months |
| 3 | 11 | M | 3 | Complex Partial | Depakote | No change | Seizure free | 17 months |
|  |  |  |  |  | Felbatol | Decreased dose |  |  |
|  |  |  |  |  | Vimpat | No change |  |  |
| 4 | 6 | F | 2 | Complex Partial | Depakote | No change | Fewer, milder and shorter seizures | 12 month |
|  |  |  |  |  | Felbatol | Increased dose |  |  |

TABLE 2-continued

The effect of PS preparation on seizures

| Subject No. | Age | Gender | Number of Anti epileptic drugs received | Epilepsy type | Concurrent AED | Effect on Drug dose | PS preparation effect at endpoint | Duration of PS preparation use |
|---|---|---|---|---|---|---|---|---|
| 5 | 16 | M | 3 | Generalized Convulsive | Depakote | No change | More seizures | 3 month |
|   |   |   |   |   | Zonisamide | No change |   |   |
| 6 | 7 | F | 2 | Complex partial | Depakote | Decreased dose | No seizures | 3 month |
|   |   |   |   |   | Felbatol | Increased dose |   |   |
|   |   |   |   |   | Trileptal | Increase dose |   |   |
| 7 | 8 | F | 1 | Generalized Non-convulsive | Zarontin | Increased dose | Fewer seizures | 5.5 month |
| 8 | 17 | M | 4 | Complex partial | Depakote | Decreased dose | Seizure free | 13 months |
|   |   |   |   |   | Primidone | Decreased dose |   |   |
|   |   |   |   |   | Onfi | Increased dose |   |   |
|   |   |   |   |   | Felbatol | Decreased dose |   |   |
| 9 | 15 | M | 3 | Complex partial | Depakote | No change | Seizure free | 11.5 months |
|   |   |   |   |   | Vimpat | No change |   |   |
|   |   |   |   |   | Felbatol | No change |   |   |
| 10 | 10 | M | 3 | Generalized Convulsive | Depakote | No change | Sleep related seizure (no change) | 3.5 month |
|   |   |   |   |   | Banzel | Decreased dose |   |   |
|   |   |   |   |   | Clobazam | Increased dose |   |   |
| *11 | 12 | F | 1 | Generalized non-convulsive | Depakote | No change | Seizure free | 14 month |
| 12 | 5 | M | 1 | Complex partial | Trileptal | Increased | Seizures | 4 month |
| 13 | 21 | F | 4 | Complex partial | Depokate | No change | No seizures | 5 month |
|   |   |   |   |   | Onfi | Increased |   |   |
|   |   |   |   |   | Trileptal | No change |   |   |
|   |   |   |   |   | Zonegran | No change |   |   |

*Baseline epilepsy status was defined as might be having seizures.

Ten out of the 13 patients (No. 1, 2, 3, 4, 6, 7, 8, 9, 11 and 13) demonstrated an improvement in their epileptic seizure state during the study period.

Of the patients who improved, patients 3, 6, 8, 9, 11 and 13 demonstrated a reduction in seizure frequency, up to a degree of seizure free/no seizures evaluation at endpoint.

Patients 4, 6, 7, 8 and 13 received an increased or mixed increased/decreased (i.e. decreased dosage of one medication and increased dosage of another at the same period of time) AED dosage and demonstrated an improvement following the co-administration with the PS preparation. For example, for patient 6, the dose of Felbatol and Trileptal increased while that of Depokate decreased, and the patient experienced improved symptoms.

Co-administration of the PS preparation of the invention with Depakote, Vimpat and Felbatol in patient No. 9 and of Depakote in patients No. 2 and 11 without modifying the dosages of these drugs resulted in an improved effect on the epilepsy status as the three patients were diagnosed as seizure free or stable.

Co-administration of Depakote, Onfi and felbatol together with the preparation resulted in an improved effect on the epileptic state, as the patient seizures were becoming milder and less frequent (patient No. 1) in comparison with the epileptic state prior to PS preparation administration. This stabilization of the patient and reduction in seizures was observed despite the reduction in Depakote dosage when co-administered with the preparation. The dose was reduced from 500 mg twice per day to one dose of 250 mg and one dose of 500 mg per day.

A similar outcome was detected when the following were combined: Depakote, Vimpat and felbatol together with the PS preparation. This combination enabled the reduction in Felbatol dose, and patient No. 3 surprisingly improved from a seizure state to a seizure free diagnosis for 17 months. The Felbatol daily dosage started at 3600 mg and was reduced to 3000 mg.

In patient No. 8 concomitant therapy of the PS preparation with Depakote, Primidone, Onfi and Felbatol had an even more pronounced effect. This combination allowed the reduction in dose of three medications: Depakote, Primidone and Felbatol and the patient's seizures were reduced to a seizure free state after 13 months of treatment. Depakote was reduced from 1500 mg to 1000 mg per day, Felbatol was reduced from 3600 mg to 3300 mg and then to 2700 mg per day, and Primidone was reduced from 250 mg to 0 mg per day. The dose of Onfi was somewhat increased.

A different scenario was demonstrated for patients No. 5, 10 and 12.

Patient No. 5, received Depakote and Zonisamide in addition to the PS preparation over a course of 3 months which did not result in an improvement of the seizure state. Patient number 10 received Depakote, Banzel and Clobazam in addition to the preparation for a course of 3.5 months. The Banzel dose was reduced from 1200 to 400 mg and the dose of Clobazam was increased from 30 mg to 40 mg. Both did not demonstrate an improvement in seizure state.

Patient No. 12 also experienced a modification in his Trileptal dose (increased from 600 to 1200 mg per day) along with administration of the PS preparation. No improvement in the extent or frequency of seizures was detected.

Patients 1, 3, 4, 6, 8, 9 and 13, diagnosed with complex partial epilepsy, and patients 2, 7 and 11, diagnosed with generalized non-convulsive epilepsy, demonstrated a greater improvement (reduction in seizures) than observed in the patients that were diagnosed with generalized convulsive epilepsy (patients 5 and 10), even though all of them consumed the same dosage of PS preparation.

Summary:

Administration of the preparation of the invention to epileptic patients, in addition to their routine medication regime, generally resulted in a reduction of seizure frequency and an improvement in the overall status of the patient.

The PS preparation of the invention was found to be effective for the majority of patients diagnosed with epileptic seizures or epilepsy, however, in patients diagnosed with complex partial epilepsy or generalized non-convulsive epilepsy, the preparation of the invention was found to be more effective than in patients that were diagnosed with generalized convulsive epilepsy, even though all of them consumed the same dosage of the preparation.

Administration of the PS preparation to epileptic patients, in addition to their routine medication regime, generally resulted in a reduction of seizure frequency and an improvement in the overall status of the patient. Co-administration of the preparation with specific anti-epileptic drugs such as Valproic acid (e.g. Depakote), and/or Felbamate (e.g. Felbatol) and/or phenobarbital and other barbiturates (e.g. primidone) resulted in a more pronounced effect in comparison with co-administration with Zonisamide, Clobazam and/or Trileptal (Oxcarbazepine).

It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination. It will also be appreciated by persons skilled in the art that the present invention is not limited by what has been particularly shown and described hereinabove.

Although the invention has been described in conjunction with specific embodiments thereof, it is evident that many alternatives, modifications and variations will be apparent to those skilled in the art. Accordingly, it is intended to additionally embrace all such alternatives, modifications and variations that fall within the spirit and broad scope of the appended claims.

What is claimed is:

1. A preparation for the treatment and/or prevention of seizures comprising a mixture of serine glycerophospholipids (PS) conjugates, wherein the mixture comprises Eicosapentaenoic acid (EPA) conjugated to PS and Docosahexaenoic acid (DHA) conjugated to PS, Palmitic acid conjugated to PS, Oleic acid conjugated to PS and Linoleic acid conjugated to PS, wherein the percentage of each of the following fatty acids: EPA, Palmitic acid, DHA, Oleic acid, and Linoleic acid attached to the PS in the preparation relative to the total fatty acids content attached to the PS in the preparation is such that the percentage of EPA is greater than or equal to the percentage of Palmitic acid, the percentage of Palmitic acid is greater than the percentage of DHA, the percentage of DHA is greater than the percentage of Oleic acid, and the percentage of Oleic acid is greater than the percentage of Linoleic acid; wherein the percentage of EPA attached to the PS in the preparation relative to the total fatty acids content attached to the PS in the preparation is greater than 18% and lower than 45%, the percentage of Palmitic acid attached to the PS in the preparation relative to the total fatty acids content attached to the PS in the preparation is greater than 14% and lower than 42%, the percentage of DHA attached to the PS in the preparation relative to the total fatty acids content attached to the PS in the preparation is greater than 6% and lower than 25%, the percentage of Oleic acid attached to the PS in the preparation relative to the total fatty acids content attached to the PS in the preparation is greater than 1% and lower than 15%, the percentage of Linoleic acid attached to the PS in the preparation relative to the total fatty acids content attached to the PS in the preparation is greater than 0.1% and lower than 6%.

2. The preparation of claim 1 wherein the ratio between (a) the percentage of EPA attached to the PS with respect to all fatty acids attached to the PS and (b) the percentage of DHA attached to the PS with respect to all fatty acids attached to the PS ((a))/(b)) is above 1.

3. The preparation of claim 1, wherein the percentage (w/w) of PS present in the preparation is greater than 10%.

4. The preparation of claim 1, wherein the percentage (w/w) of PS relative to the total phospholipids in the preparation is greater than 20%.

5. The preparation of claim 1, further comprising phosphatidic acid and lysophosphatidic acid, wherein the ratio by weight of the PS in the preparation relative to the total weight of phosphatidic acid and lysophosphatidic acid in the preparation is greater than 1:1 and lower than 10:1.

6. The preparation of claim 1, wherein the percentage of EPA attached to the PS in the preparation relative to the total fatty acids content attached to the PS in the preparation is greater than 22% and lower than 40%.

7. The preparation of claim 1, wherein the percentage of Palmitic acid attached to the PS in the preparation relative to the total fatty acids content attached to the PS in the preparation is greater than 18% and lower than 40%.

8. The preparation of claim 1, wherein the percentage of DHA attached to the PS in the preparation relative to the total fatty acids content attached to the PS in the preparation is greater than 8% and lower than 22%.

9. The preparation of claim 1, wherein the percentage of Oleic acid attached to the PS in the preparation relative to the total fatty acids content attached to the PS in the preparation is greater than 2% and lower than 13%.

10. The preparation of claim 1 wherein the percentage of Linoleic acid attached to the PS in the preparation relative to the total fatty acids content attached to the PS in the preparation is greater than 0.5% and lower than 4%.

11. The preparation of claim 1, further comprising an anti-seizure drug.

12. The preparation of claim 11, wherein the anti-seizure drug is an AED (anti-epileptic drug).

13. The preparation of claim 12, wherein said AED is Valproic acid, Felbamate, phenobarbital or any other barbiturate.

14. The preparation of claim 2, wherein the (a)/(b) ratio is from about 1.1 to about 3.

15. The preparation of claim 2, wherein the (a)/(b) ratio is from about 1.5 to about 3.

16. A method for treating seizures in a subject, comprising administering the preparation of claim 1 to a subject in need thereof.

17. The method of claim 16, comprising administering an AED simultaneously with the preparation.

18. The method of claim 16 comprising administering an AED separately from the preparation.

19. The method of claim 17, wherein the AED is Valproic acid, Felbamate, phenobarbital or any other barbiturate.

20. The method of claim 16, wherein said seizures are classed as complex partial epileptic seizures or generalized non-convulsive epileptic seizures.

21. The method of claim 18, wherein the AED is Valproic acid, Felbamate, phenobarbital or any other barbiturate.

* * * * *